(12) United States Patent
Jafri

(10) Patent No.: US 11,890,249 B2
(45) Date of Patent: Feb. 6, 2024

(54) MEDICAL DEVICE FOR CONSTRICTING VENOUS OUTFLOW AND FOR PROVIDING VIBRATORY STIMULUS

(71) Applicant: Maqsood Jafri, Edwardsville, IL (US)

(72) Inventor: Maqsood Jafri, Edwardsville, IL (US)

( * ) Notice: Subject to any disclaimer, the term of this patent is extended or adjusted under 35 U.S.C. 154(b) by 421 days.

(21) Appl. No.: 15/355,223

(22) Filed: Nov. 18, 2016

(65) Prior Publication Data

US 2017/0135895 A1 May 18, 2017

Related U.S. Application Data

(60) Provisional application No. 62/391,588, filed on May 3, 2016, provisional application No. 62/386,086, filed on Nov. 18, 2015.

(51) Int. Cl.
| | | |
|---|---|---|
| *A61H 19/00* | (2006.01) | |
| *A61F 5/41* | (2006.01) | |
| *A61H 9/00* | (2006.01) | |
| *A61H 23/02* | (2006.01) | |

(52) U.S. Cl.
CPC .............. *A61H 19/32* (2013.01); *A61F 5/41* (2013.01); *A61H 9/0057* (2013.01); *A61H 9/0078* (2013.01); *A61H 23/02* (2013.01); *A61F 2005/411* (2013.01); *A61F 2005/414* (2013.01); *A61F 2005/415* (2013.01); *A61F 2005/417* (2013.01); *A61H 2201/5071* (2013.01)

(58) Field of Classification Search
CPC .......... A61F 2005/411; A61F 2005/414; A61F 2005/415; A61F 2005/417; A61F 5/41; A61H 19/32
See application file for complete search history.

(56) References Cited

U.S. PATENT DOCUMENTS

| | | | | |
|---|---|---|---|---|
| 4,641,638 A | * | 2/1987 | Perry | A61F 5/41 600/39 |
| 4,672,954 A | * | 6/1987 | Panzer | A61F 5/41 600/39 |
| 6,569,083 B1 | * | 5/2003 | Kassman | A61F 5/41 128/842 |

(Continued)

FOREIGN PATENT DOCUMENTS

| | | | |
|---|---|---|---|
| WO | WO-9715251 A1 * | 5/1997 | ............... A61F 5/41 |
| WO | 2004084779 A1 | 10/2004 | |

*Primary Examiner* — Christine H Matthews
(74) *Attorney, Agent, or Firm* — Williams Intellectual Property

(57) ABSTRACT

An apparatus for constricting blood flow and for providing vibratory stimulus to address erectile dysfunction includes a single vibration unit or multiple vibration units. One embodiment includes proximal and distal rings or bands configured to annularly surround a penis close to the base of the penis and proximal to the glans. In another embodiment, the annular rings or bands are connected by at least one intermediate bar, which houses vibratory units, and/or at least one splint which may be an inflatable splint. The intermediate bar is configured to partially cover a penis between the bands. The device is made of an elastic, skin-compatible, slippery/smooth material. The apparatus may include use of a vacuum tube, to induce an erection, and an inflatable constriction ring to maintain the erection induced.

44 Claims, 10 Drawing Sheets

(56) References Cited

U.S. PATENT DOCUMENTS

| | | | |
|---|---|---|---|
| 6,659,938 B1* | 12/2003 | Orlowski | A61F 5/41 600/38 |
| 2006/0229494 A1 | 10/2006 | Wu | |
| 2007/0093686 A1* | 4/2007 | Dykers, Jr. | A61F 5/41 600/38 |
| 2011/0172489 A1 | 7/2011 | Muller | |
| 2014/0171734 A1 | 6/2014 | Kassman | |
| 2015/0141748 A1* | 5/2015 | Campbell | A61H 19/32 600/38 |

* cited by examiner

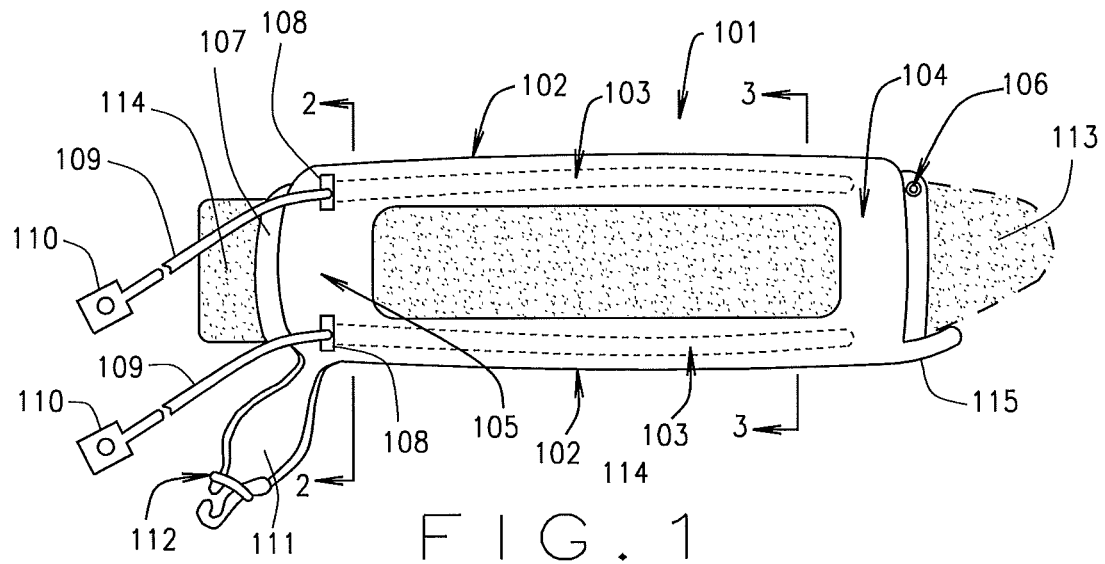
FIG. 1
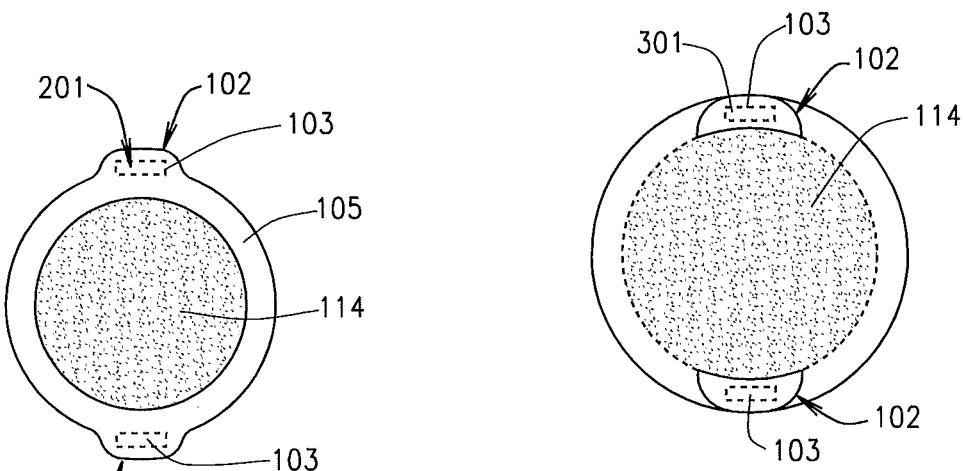
FIG. 2
FIG. 3
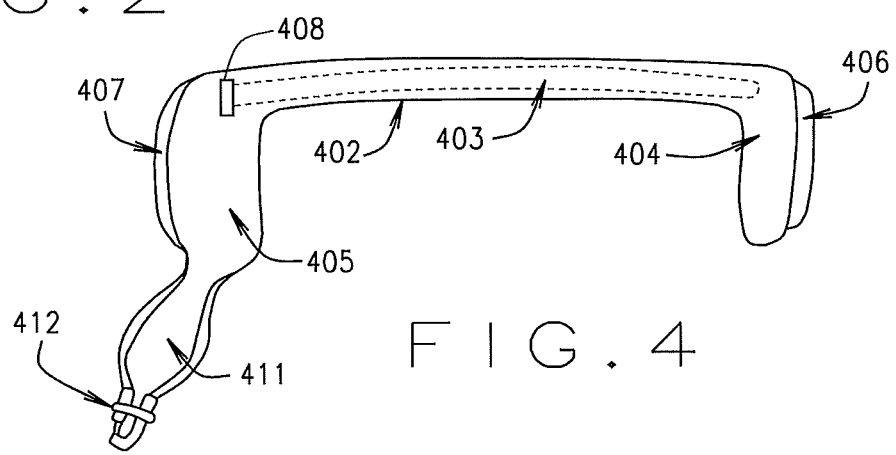
FIG. 4

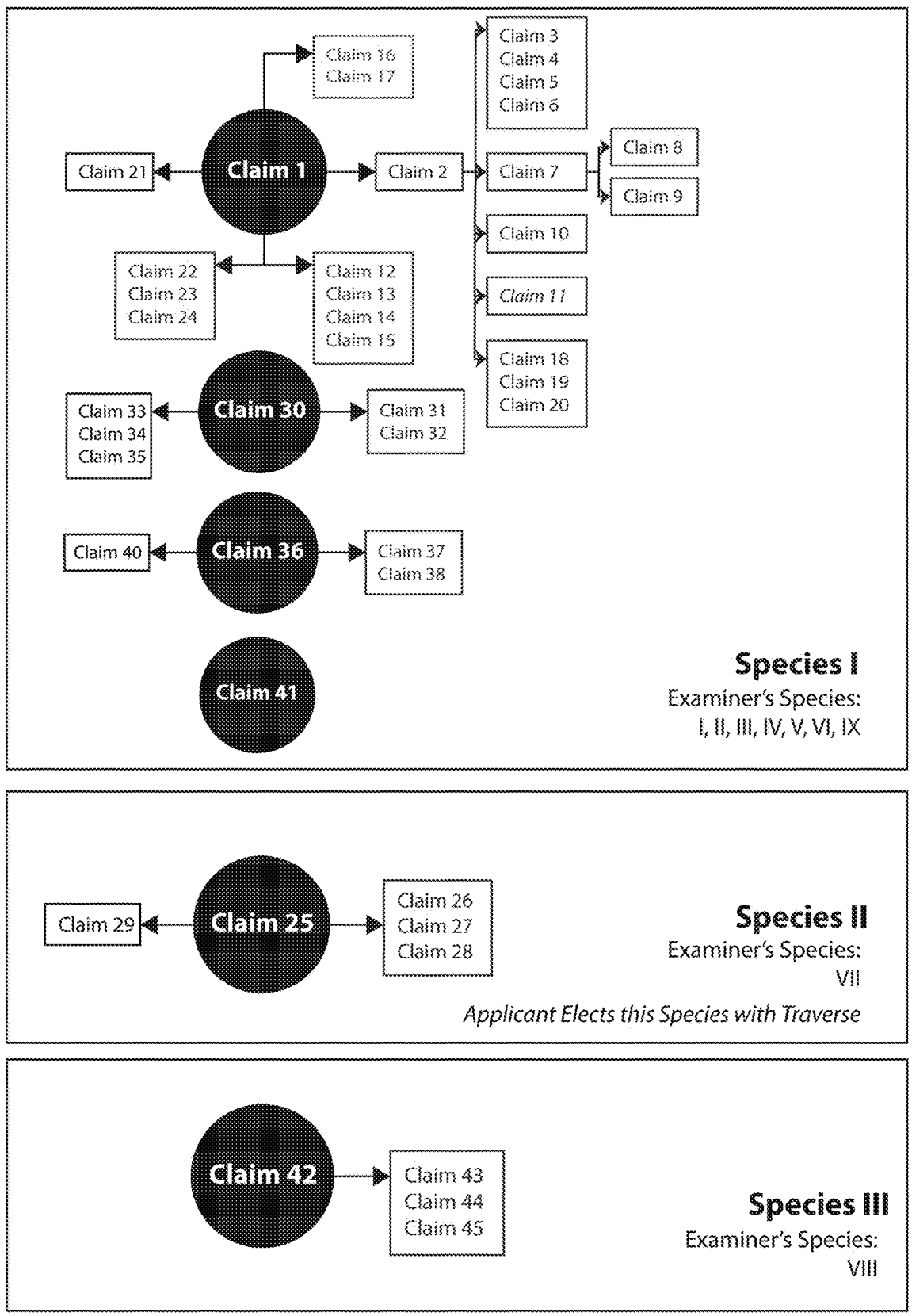
FIG. 2 - Claims Grouped by Species Identified by Applicant

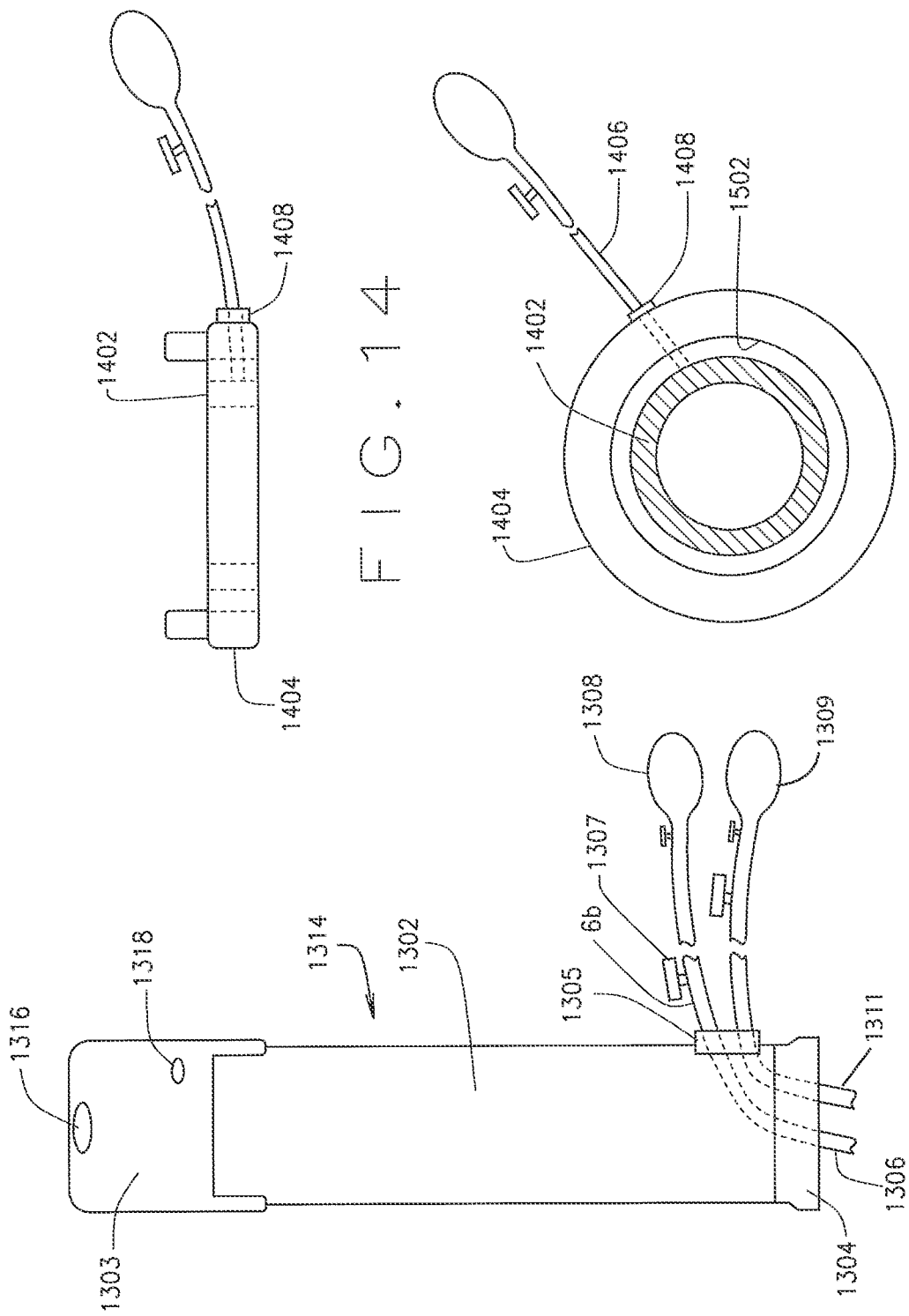

MEDICAL DEVICE FOR CONSTRICTING VENOUS OUTFLOW AND FOR PROVIDING VIBRATORY STIMULUS

Cross Reference: This application claims priority to and the benefit of provisional application Ser. No. 62/391,588 filed on May 3, 2016 and entitled Mechanical & Vibratory Device In Combination With Inflatable Constriction Device For Treatment Of Erectile Dysfunction and Penile Rehabilitation; and provisional application Ser. No. 62/386,086 filed on Nov. 18, 2015 and entitled Mechanical & Vibratory Devices In Combination With Inflatable Constriction Device For Treatment Of Erectile Dysfunction and Penile Rehabilitation.

BACKGROUND

FIELD: This technology as disclosed herein relates generally to medical devices and, more particularly, to medical devices to address erectile dysfunction.

BACKGROUND: Erectile dysfunction is a medical condition that impacts men. The medical disorder can be manifested as the inability to obtain and/or sustain an erection. Various devices have been utilized to induce an erection including vibratory devices and vacuum tube devices. Also, various devices have been utilized to sustain an erection including constriction devices. However, many of the devices available are cumbersome and impractical or don't adequately address the problem, particularly in the more severe cases of the disorder. A more practical and effective medical device is needed to address this common dysfunction.

SUMMARY

The technology as disclosed herein includes an apparatus for constricting blood flow and for providing vibratory stimulus to address erectile dysfunction. One implementation of the technology for enhancing erectile function includes a single vibration unit or multiple vibration units. One implementation of the technology includes proximal and distal annular bands configured to annularly surround a penis close to the base of the penis and proximal to the glans. For one implementation of the technology, the two annular bands are connected by means of single or multiple elongated intermediate bars which house vibratory units. The intermediate bars are configured to partially cover a penis between the bands during use. One implementation of the device is made of an elastic, skin-compatible, slipper/smooth material.

One implementation of the technology as disclosed and claimed herein can be utilized in combination with a vacuum based erection-inducing device. An erection-inducing vacuum inflatable constriction device (VICD) is designed to address erectile dysfunction. The technology can include a vacuum chamber, which has a distal end for connection to a manual or battery powered vacuum generating device. The technology further includes a pliable constriction ring which can be an inflatable constriction device (ICD) to be positioned at the base of the penis. The vacuum chamber includes length markings for the user to record length.

One implementation of the technology as disclosed and claimed herein can be used in combination with an implanted penile prosthesis device. Placement of an implant is an effective method for treating erectile dysfunction, however it does interfere with the physiology of the corpora that may still have functional erectile tissue, and implants do not extend into the glans of the penis. The cavernosal erectile tissue and glans continue to suffer from underlying hemodynamic dysfunction and do not engorge fully, therefore, and remain soft and cold, giving rise to concord tip deformity in the case of the glans. This can be addressed by pharmacological/mechanical means that will make the penis look and feel normal, thermally and otherwise.

The technology as disclosed and claimed herein will help to retain an erection. The Inflatable Constriction Device (ICD) as disclosed and claimed herein can be utilized in combination with a penile prosthesis device. The technology as disclosed and claimed includes inflatable proximal and distal rings, an inflation pump and tubing system, and an intermediate bar having a micro-channel for providing an air passage for inflation of a distal inflatable ring.

Another implementation of the technology is its use as an external penile prosthesis, which includes proximal and distal annular bands attached to the proximal and distal inflatable constriction rings configured for encircling an anatomically elongated tubular structure. The rings are configured to be inflatable by air and/or liquid. The annular bands are connected by an intermediate single bar or multiple bars. For one implementation of the technology the intermediate bars have a support mechanism in the form of single or multiple stiff bars, which can be flexible or rigid. In yet another implementation, the support is provided in the form of external inflatable "splint" mechanism as well. The technology as disclosed is suitable for the patient who is able to have an erection but cannot maintain it or does not want to use a vibrator or a vacuum inflatable constriction device (VICD).

The device according to the disclosure herein includes a proximal and distal annular band-like structure by means of which the device completely surrounds a preferably tubular and elongate anatomical body at a proximal and a distal end thereof. At least one intermediate bar extends between the two annular bands. The at least one intermediate bar includes a single bar for one implementation but can include two or more bars in a multiple bar configuration. For one implementation of the technology, a splint is integrated within the device longitudinally within the intermediate bar along substantially the entire length of the intermediate bar, thereby providing support along substantially the entire length of the penis. The device includes an elastic, skin-compatible and smooth material.

One implementation of the technology as disclosed and claimed herein includes an external vibratory device. A vibratory device can be utilized to induce an erection by means of vibration forces being applied to the penis of a user and stimulating the nerves (Dorsal Nerve and Perineal Nerve and Cavernous Nerve for example). The device can be used for penile rehabilitation and can be used by an individual with erectile dysfunction who needs or prefers to use vibration but does not want to wear the vibratory device during intercourse. These patients can often attain an erection by using vibratory stimulation but may or may not need additional assistive devices to induce or maintain an erection. This device can further be used for ejaculation in paraplegic patients.

One implementation of the technology includes an external vibrator which includes multiple longitudinal bands of flexible skin-compatible material. The longitudinal bands may house vibratory units in a longitudinal fashion, extending substantially along the entire length of the penis to directly provide stimulation thereto. The vibratory units are replaceable by extracting each vibratory unit through a slit in the band or inserting a vibratory unit through the slit. The dorsal/dorsolateral vibratory unit overlies the dorsal/dorsolateral area of the penis and stimulates the penile skin and the dorsal nerve, and the ventral vibratory unit overlies the urethral area and stimulates skin and the perennial nerve. An extension in the ventral area can be provided to stimulate the frenulum. A user can hold the device and press it against the penis to help impart the vibration.

The features, functions, and advantages that have been discussed can be achieved independently in various implementations or may be combined in yet other implementations further details of which can be seen with reference to the following description and drawings.

These and other advantageous features of the present technology as disclosed will be in part apparent and in part pointed out herein below.

BRIEF DESCRIPTION OF THE DRAWINGS

For a better understanding of the present technology as disclosed, reference may be made to the accompanying drawings in which:

FIG. 1 is a side view of the device showing vibratory units;

FIG. 2 is cross section through the proximal annular band;

FIG. 3 is a cross section through the intermediate bars;

FIG. 4 is a side view of the device with a single top intermediate bar;

FIG. 13 C is inflatable constriction ring;

FIG. 14 is a side view of a coaxial constriction ring disposed in relation to a seal;

FIG. 15 is a bottom view of the coaxial constriction ring disposed inside the seal;

Figure 5:
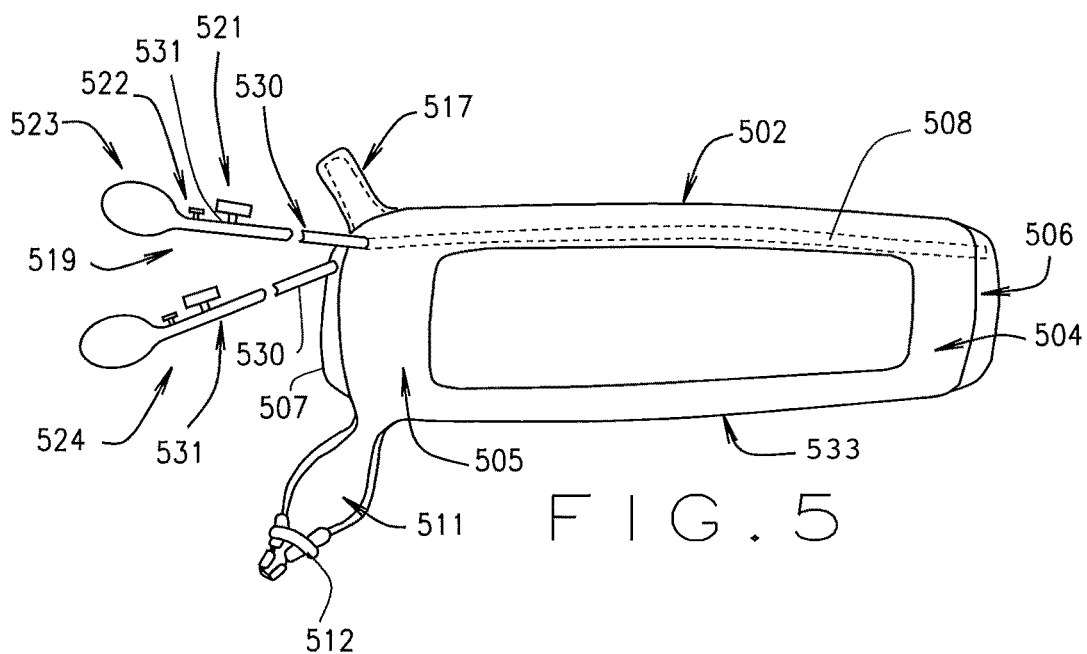
FIG. 5 is a side view of one implementation of the device showing the inflation mechanism.

While the technology as disclosed is susceptible to various modifications and alternative forms, specific implementations thereof are shown by way of example in the drawings and will herein be described in detail. It should be understood, however, that the drawings and detailed description presented herein are not intended to limit the disclosure to the particular implementations as disclosed, but on the contrary, the intention is to cover all modifications, equivalents, and alternatives falling within the scope of the present technology as disclosed and as defined by the appended claims.

DESCRIPTION

According to the implementation(s) of the present technology as disclosed, various views are illustrated in FIG. 1-20 and like reference numerals are used consistently throughout to refer to like and corresponding parts of the technology for all of the various views and figures of the drawing. Also, please note that the first digit(s) of the reference number for a given item or part of the technology should correspond to the Fig. number in which the item or part is first identified.

One implementation of the present technology as disclosed comprises an inflatable constrictive band and a vibratory unit that teaches a novel apparatus and method for addressing erectile dysfunction. The technology includes proximal and distal annular band structure configured to surround an elongate anatomical body part, such as a penis, annularly at proximal and distal ends. With one implementation of the technology, an elongated intermediate bar extends between the proximal and distal annular band structures. In another implementation of the technology, there can be multiple elongated intermediate bars extending between the proximal and distal annular band structures.

The intermediate bars have sufficient length such that the proximal annular band can be positioned at the base of a penis proximate a user's abdomen and scrotum and the distal annular band can be positioned proximate the base of the glans of the user. The length of the intermediate bar, or bars, can vary depending on the anatomy of the user. At least one vibration unit is integrated within, or housed within, the device extending longitudinally and substantially along the entire length of each at least one intermediate bar. Each vibratory unit positioned within each at least one intermediate bar, extending substantially along the entire length of each at least one intermediary bar, allows the device to impart vibration to almost the entire length of penis directly. One implementation of the technology as disclosed includes an elastic, skin-compatible and smooth/slippery material on the outside.

The intermediate bar can extend beyond the distal annular band along the ventral area to stimulate the frenulum of prepuce of penis (frenulum), which is an elastic band of tissue under the glans that connects the foreskin (prepuce) to the vernal mucosa. One implementation of the technology includes stretchable and pliable smaller ring-like structures attached to the proximal and distal annular bands to help prevent venous outflow and also to help keep the device in position. These ring-like structures preferably have non-slippery inner surfaces.

One implementation of the technology as disclosed and claimed includes inflatable constriction rings in lieu of the stretchable smaller ring-like structures attached to the proximal and distal annular bands as described to control venous outflow and, as a secondary benefit, help anchor the device to the penis. Venous outflow is a significant factor in causing erectile dysfunction in many middle aged and most elderly patients and in selected patients of a younger age.

One implementation of the constriction ring includes an inflatable ring structure having an interior bladder communicable with an inflation system and a pliably expandable wall structure containing the interior bladder and forming a ring structure. A proximate inflatable annular ring is configured to encircle the base of penis and a distal inflatable ring is configured to encircle the base of the glans.

One implementation of the outer surface of the inflatable ring opposite the side that contacts the penis of is made of non-resilient material. The inner surface that contacts the penis is made of skin compatible, preferably non-slippery material. Any material can be used that will allow for inflation to provide constriction. This proximate and distal inflatable ring can be inflated by air or liquid. The inflation system is communicable with the interior bladder and is configured to push a flow of air or liquid to fill the bladder and expand at least the inner surface of the inflatable ring to thereby reduce its diameter and apply an inward pressure against the penis to constrict blood flow.

One implementation of the inflatable constriction ring includes a manual or battery operated mini-pump having an outlet port through which air or fluid is forcibly pumped. The outlet port of the mini-pump, in one implementation, is communicably connected to the interior bladder by a tube. The mini-pumps are attached to the inflatable constriction rings by detachable tubing either directly to the inflatable ring or by means of small tubing attached to the annular band above the ring.

One implementation of the proximal and distal constriction rings includes an ear-like structure to assist with placing the ring around the penis and removing the ring from the penis. If the technology is utilized in combination with a vacuum chamber, as will be discussed further, the ends of the ear-like structure can be placed inside the sealing end of the vacuum chamber to assist with holding the ring in position while evacuating the vacuum chamber if so desired.

One implementation of the proximal and distal inflatable constriction rings includes projections on the inner surface that cover and apply pressure to dorsal and dorsolateral parts of the penis corresponding to the position of the penile veins whereby the rings can apply continuous pressure to constrict venous out-flow through the veins. Such dorsolateral pressure may impede the arterial flow in dorsal arteries in patients who require high pressure in the ring to control venous outflow. In this situation, just one dorsal projection may be more beneficial to compress the dorsal vein.

One implementation of the proximal and distal inflatable constriction rings includes projections on the inner surface at dorsolateral and ventrolateral positions to compress the corpora cavernosa diagonally and impede venous outflow from the corpora cavernosa. One implementation of the proximal and distal inflatable constriction ring includes projections of different shapes on the inner surface at lateral positions to compress the corpora cavernosa from the sides to impede venous outflow from the corpora cavernosa.

With one implementation the proximal and distal inflatable rings have a groove at the position corresponding to the area of the urethra. The groove can be used in combination with the projections. However, the distal inflatable ring may only include a groove for to accommodate the urethra. The groove is kept in place when inflation occurs by reinforcing ventral ends with a stiffening material/mechanism. The end of the ring in the urethral area of the penis is reinforced with stifling material and a stiff bar member bridges the gap between the two stiff non-contacting ends of the ring. Two attachments obliquely attached between the end of the ring and the stiff bar further anchor the ends of the ring to the bar to prevent ends of the ring pushing inwards dorsally. The groove allows the free passage of ejaculate, however, the groove may allow venous outflow from the corpus spongiosum causing loss of erection, particularly from the glans.

For one implementation, to address the above problem, the urethral groove may be eliminated and replaced with a bulge or cushion at the corpus spongiosum position. With this implementation, deflation of the inflatable ring is effected by manually operating or controlling remotely the inflation system to facilitate natural ejaculation. Similarly this implementation may be utilized for both the proximal and distal constriction rings. The tubing of the inflation system is connected to the outer surface of each inflatable constriction ring. The tubing of the inflation system, connected to the distal constriction ring, is attached by means of a micro-channel running through the intermediate bar to serve as a fluid communication conduit between the tubing and the interior bladder of the inflatable constriction ring.

The tubing that attaches to the inflatable mini-pumps has a detachment mechanism close to the proximal inflatable constriction ring and the part of the tubing that remains attached to the inflatable constriction ring also has a deflation release valve that can be used to deflate the inflatable constriction ring after use. One implementation of the tubing directly attaches to the inflatable ring. In this embodiment, the proximal inflatable constriction ring and the distal constriction ring each have a pressure release valve. The constriction ring is also deflatable by connecting the detached tubing and using the release valve of the mini-pump.

After inflating the inflatable constriction rings optimally the tubing is detached and the part of the tubing attached to the constriction rings is stored in a small pocket attached to one of the rings to prevent injury from the loose end during intimate contact. The tubing of the inflation system for the inflatable constriction ring also has pressure measuring gauge to measure the pressure in the inflatable constriction ring. The proximal constriction ring, especially with the cushion at the corpus spongiosum position, may be enough to maintain erection of the corpora cavernosa and corpus spongiosum/glans; therefore, in such embodiments, the distal inflatable constriction ring mechanism may not be necessary.

A significant advantage of the invention is that the vibration unit/units are completely housed in the device extending almost the entire length of the device so that the device imparts vibration directly to penis and penile nerves along almost the entire length of the penis. However, single or multiple vibratory units can be inserted at the base of the penis or at the frenulum region for applying vibrations for a short distance for people with a mild erectile problem with or without stiffened intermediate bars.

One implementation of the technology includes a battery for powering the vibratory unit and the battery can be integral with the vibratory unit. The vibratory unit can be switched on and off and the intensity or amplitude of the vibration force can be selectively and variably adjusted remotely with a control unit by transmitting a signal from the control unit to the vibratory unit via a communication wire or by way of wireless connectivity. The battery or other power source can also be remotely connected to the vibratory unit by means of a cable. With one implementation, the vibratory unit can include a battery container that also has a control that controls the unit to switch it on and off and adjust the intensity of the vibrations. In one implementation the battery/power source with control mechanism is placed in the wireless remote control unit.

Various implementations of the vibration unit include one or more of a piezoelectric vibrator, an eccentric rotating mass vibrator, a linear resonant actuator vibrator or any other appropriate type of vibrator. One implementation of a vibratory unit allows for easy replacement and includes an opening in the annular band that opens to an interior channel of the intermediate bar into which a vibratory unit is installed and through which a vibratory unit is removed. The vibratory unit can be removed through the opening that can be covered with water tight cover. Alternatively, vibratory units can be placed permanently in the intermediate bar, especially where remote power or long-life power sources are contemplated.

One implementation of the technology includes a stretchable beaded ring attached on the proximal annular band of the device. The stretchable beaded ring is configured to be extended about the testicles (scrotum) to thereby further secure the device in place. A small tightening ring is threaded over the beaded ring to tighten or loosen the beaded ring about the scrotum. This arrangement provides additional support for the main device and also imparts vibration to the scrotum. The device can be held against the flaccid penis by collapsing the flexible device with the hand and urging the vibrators in contact with the penis causing stimulation of one or more penile surfaces and associated nerve endings of the dorsal nerve/perineal nerve that can assist with attaining and maintaining an erection. The patient can continue to wear the device throughout intercourse.

As a result of the stiffness imparted by the vibratory units longitudinally encased in flexible, skin-compatible material, coupled with the effect of vibration to enhance penile blood flow to help achieve erection, the device can provide an erection for successful intercourse for individuals with erectile dysfunction.

The devices can be used in combination with a Vacuum Inflatable Constriction Device (VICD), designed for achieving and maintaining an erection, which is separately described herein. The device can also be used alone or in combination with other devices. An added advantage of the device is that it increases the circumference of the penis over almost the entire length of the penis.

The details of the technology as disclosed and the various implementations contemplated may be better understood by referring to the accompanying figures. Referring to FIG. 1, a side view of the device 101 is shown. The technology as shown in FIG. 1 includes, a proximal annular band 105 and a distal annular band 104. Intermediate bars 102 extend between and connect the proximate and distal annular bands 105, 104. The intermediate bars house vibratory units 103 which extend longitudinally substantially along the entire length of the intermediate bars 102. Therefore, the vibratory units 103 will extend longitudinally substantially along the entire length of the penis. In other implementations, three or even four intermediate bars can extend between the annular bands, each housing vibratory units 103. The device is configured such that it can be installed to position the distal annular band 104 to encircle the penis proximate to the glans 113. The device is also configured such that it can be installed to position the proximal annular band 105 to encircle the base area 114 of the penis proximal to the abdomen and scrotum of the user. The distal inflatable constrictive ring 106 is sized and configured to encircle the penis at the base of the glans 113. The proximal inflatable constrictive ring 107 is configured to encircle the penis close to base 114 of the penis.

A slit (or opening) 108 is included in the proximal annular band 105, which opens to an elongated interior channel of an intermediate bar 102 such that a vibratory unit 103 is insertable through the opening 108 and into the elongated interior channel 201 whereby the vibratory unit 103 is housed in the elongated intermediate bar 102 and extends longitudinally along substantially the entire length of the elongated intermediate bar 102. The slit (or opening) 108 is configured for the insertion of the vibratory unit 103 with cable 109 passing through the opening for communication with, and conveying power to, the vibratory unit 103. An external remote control system 110 is configured to house and accommodate a battery or other power source for the vibratory unit 103 along with a controller. The cable 109 is configured for power and communication transmission. The battery and the control function can be built into the same unit 110. A stretchable beaded ring 111 is attached on the proximal annular band 105 of the device. The stretchable beaded ring 111 is configured to be extended about the testicles (scrotum) to thereby further secure the device. A small tightening ring 112 is threaded over the beaded ring 111 to tighten or loosen the beaded ring 111 about the scrotum. This arrangement provides additional support for the main device and also imparts vibration to the scrotum. The patient can continue to wear the device throughout intercourse. The glans 113 and portions of the penis are exposed. The frenulum extension 115 is also illustrated. The intermediate bars 102 can have an extension 115 beyond the distal annular band 104 along the ventral area of the penis to stimulate the frenulum of prepuce of penis (frenulum), which is an elastic band of tissue under the glans that connects the foreskin (prepuce) to the vernal mucosa. The device can be worn in a different fashion depending on the individual. The upper elongated intermediate bar as shown in FIG. 1, in one implementation, is configured to extend along the dorsal area of the penis and the opposing lower elongated intermediate bar as shown can extend along the ventral area of the penis.

Referring to FIG. 2, a cross section through the proximal annular band 105 is provided. The interior channel 201 of the intermediate bars 102 that extends from the opening 108 and contains the inserted vibratory units 103 is illustrated. One implementation of the technology can include two vibratory units 103 positioned at the dorsal and/or dorsolateral positions. Vibratory units 103 positioned in the dorsal and/or dorsolateral positions will stimulate the dorsal nerve branches in the penis. The proximal annular band 105 is configured to encircle the base 114 of the penis when being utilized. Referring to FIG. 3, a cross section through the intermediate bars 102 proximate to the distal annular band 104 is illustrated. Again, the interior channel 301 of the intermediate bars 102 that contains the inserted vibratory units 103 are illustrated. The outline of the distal annular band 104 is also seen. Note that with the implementation in-use as shown, the side portions of the penis are exposed and the intermediate bars 102 extend over the top and bottom areas of the penis.

Referring to FIG. 4, a side view of the device with a single top intermediate bar 402 is illustrated, which houses a vibratory system 403. The intermediate bar 402 extends between and connects the proximal annular band 405 and the distal annular band 404. The technology as shown in FIG. 4 includes a proximal annular band 405 and a distal annular band 404. The intermediate bar 402 house vibratory system 403 which extends longitudinally substantially along the entire length of the intermediate bar 402. Therefore, the vibratory system 403 will extend longitudinally substantially along the entire length of the penis. In other implementations, three or even four intermediate bars 402 can extend between the annular bands 404, 405, each housing a vibratory system 403. The device is configured such that it can be installed to position the distal annular band 404 to encircle the penis proximate to the glans 113. The device is also configured such that it can be installed to position the proximal annular band 405 to encircle the base 114 area of the penis proximate to the abdomen and scrotum of the user. The distal inflatable constrictive ring 406 is sized and configured to encircle the penis at the base of glans 113. The proximal inflatable constrictive ring 407 is configured to encircle the penis proximate the base 114 of penis.

A slit (or opening) 408 is included in the proximal annular band 405, which opens to an elongated interior channel of an intermediate bar 402 wherein the vibratory system 403 is insertable through the opening 408 and into the elongated interior channel. The slit (or opening) 408 is configured for insertion and placement of the vibratory system 403 with cable passing through the opening 408 for communication with and providing power to the vibratory system 403. An external remote control system can be utilized and can be configured to house and accommodate a battery or other power source for the vibratory system 403 along with a controller. A cable can be configured for power transmission and to operationally communicate with the device. The battery and the control function can be built into the same unit. A stretchable beaded ring 411 is attached on the proximal annular band 405 of the device. The stretchable beaded ring 411 is configured to be extended about the testicles (scrotum) to thereby further secure the device. A small tightening ring 412 is threaded over the beaded ring 411 to tighten or loosen the beaded ring 411 about the scrotum. This arrangement provides additional support for the main device and also imparts vibration to the scrotum. The patient can continue to wear the device throughout intercourse. The device can be worn in a different fashion depending on the individual. The device can be worn with rearrangement or elimination of stretchable beaded ring 411. The vibratory system 403 can be large enough to cover both dorsal nerves or, alternatively, two separate vibratory systems 403 can be placed dorsally/dorsolaterally.

Figure 6:
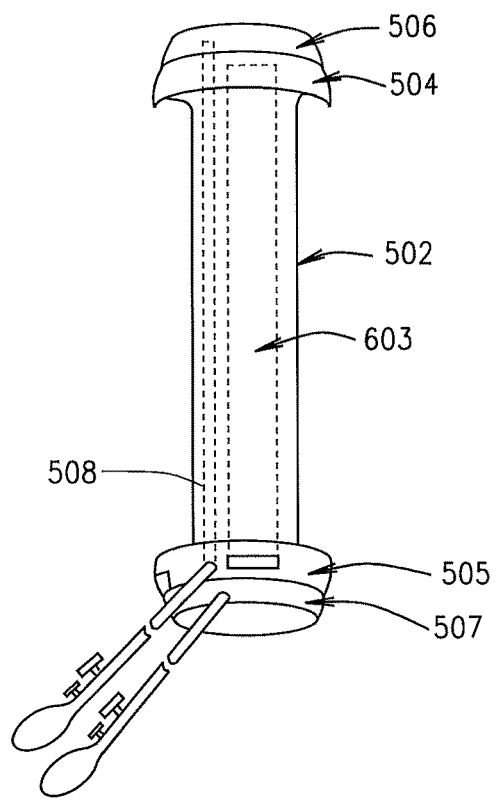
FIG. 6 is atop view of one implementation of the device showing the inflation mechanism and dorsal vibrator.

Referring to FIGS. 5 and 6, side and top view of one implementation of the device is illustrated with microchannel 508 and vibratory unit 603. FIG. 5 predominantly illustrates an inflation system for the proximal 507 and distal 506 inflatable constrictive rings. A pocket 517 for storage of inflation tubing 530 is provided so that loose tubing is stowed to avoid discomfort. A microchannel 508 extends through the intermediate bar 502 as a fluid passageway to transmit air or other fluid to inflate the distal inflatable constriction ring 506. FIG. 5 also shows additional intermediate bar 533.

One implementation of the technology includes an inflation system 519 for the distal inflatable constriction ring 506. The inflation tubing consists of two parts 530 and 531. Tubing 530 and 531 is detachable after attaining optimum pressure in the inflatable constriction rings 506, 507 and tubing 530 is storable in the pocket 517. A release valve is located on 531 or on the inflatable ring. Deflation of the inflatable constriction rings 506, 507 can also be achieved by connecting 531 tubing and using the deflation knob 522. One implementation of the technology may include a pressure measuring gauge 521. One implementation may include a deflation knob 522 to adjust the pressure. A manual inflation pump 523 is illustrated. There is also an inflation system 524 for the proximal constriction ring 507. The mechanical inflation/deflation system in one implementation is a motorized inflation/deflation system.

Referring to FIG. 6, top view is illustrated with one implementation of the device with vibratory unit 603. The elongated vibratory unit 603 extends along a dorsal position. However, one implementation of the technology may include dual vibratory units positioned at the dorsal and/or dorsolateral position (not shown). Vibratory units positioned in the dorsal and/or dorsolateral positions will stimulate the nerves along these areas of the penis. A micro-channel 508 is illustrated that extends through the intermediate bar 502 and is used as a fluid passageway to transmit air or other fluid to inflate the distal constriction ring 506.

Figure 7:
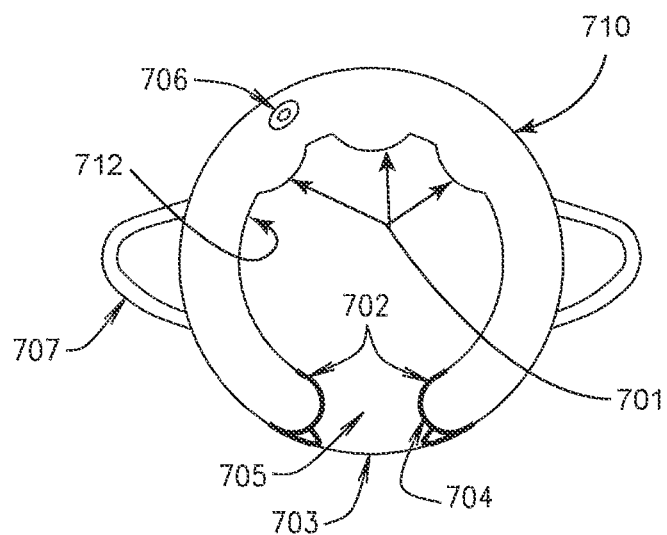
FIG. 7 is constriction ring with dorsal and dorsolateral projections.

Referring to FIG. 7, one implementation of the constriction rings includes an inflatable ring-like structure having an interior bladder communicable with an inflation system and a pliably expandable wall structure containing the interior bladder and forming a ring-like structure. A proximate inflatable annular ring is configured to encircle the base of penis and a distal inflatable ring is configured to encircle the base of glans.

One implementation of the outer surface 710 that is opposite of the side 712 that contacts the penis of such inflatable ring is made of non-resilient material and inner surface that contacts the penis is made of skin compatible preferably non-slippery material. Any material can be used that will allow for inflation to provide constriction. This proximate and distal inflatable ring can be inflated by air or liquid. The inflation system that is communicable with the interior bladder is configured to push a flow of air or liquid to fill the bladder and expand at least the inner surface of the inflatable ring to thereby reduce its diameter and apply an inward pressure against the penis to constrict blood flow.

One implementation of the inflatable constriction ring includes a manual or battery operated mini-pump having an outlet port through which air or fluid is forcibly pumped. The outlet port of the mini-pump, in one implementation, is communicably connected to the interior bladder by a tube, where the tube communicably attaches to port 706, which is communicable with the interior bladder. The mini-pumps are attached to the inflatable constriction rings by detachable tubing either directly to the inflatable ring or by means of small tubing attached to the annular band above ring, which has a conduit communicable with port 706.

One implementation of the proximal and distal constriction rings includes an ear-like structure 707 to assist with placing the ring around the penis and removing the ring. If the technology is utilized in combination with a vacuum chamber, as will be discussed further, the ends of the ear-like structure can be placed inside the sealing end of the vacuum chamber to assist with holding the ring in position while evacuating the vacuum chamber if so desired.

Figure 20A:
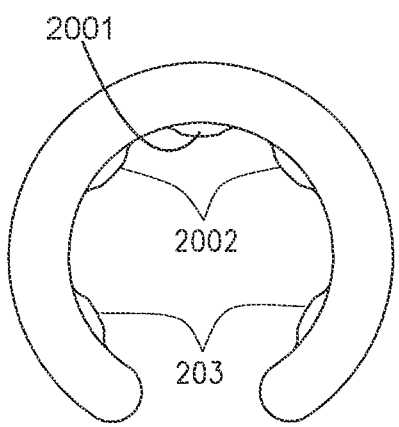
FIGS. 20A, 20B and 20C are various constriction ring implementations.

One implementation of the proximal and distal inflatable constriction ring includes projections 701 on the inner surface that cover and apply pressure to the dorsal and dorsolateral position of the penis at the base corresponding to the position of the penile veins. One implementation, as reflected in FIG. 8 has a continuous cushion 801 covering the dorsal and dorsolateral position of the penis to thereby apply a continuous pressure to constrict blood flow through the blood carrying vessels in these areas. The cushion at the dorsolateral position may impede the arterial flow in dorsal arteries in patients requiring high pressure in the ring to control a venous leak problem. In this situation, just one dorsal cushion may be more beneficial to compress the dorsal vein. The projection may be eliminated in the case of the distal constriction ring. One implementation of proximal inflatable constriction ring is shown in FIG. 20A. Dorsolateral projections 2002 and ventrolateral projections 203 compress the base of the penis diagonally to impede venous outflow from corpora cavernosa. One implementation of the proximal inflatable constriction ring shown in FIG. 20 B, includes lateral projections 2004 to compress the base of the penis to impede venous outflow from the corpora cavernosa from the sides. FIG. 20C provides a different shape of lateral projection 2006.

Figure 8:
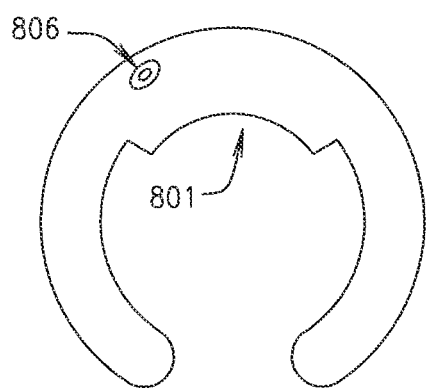
FIG. 8 is a constriction ring with a dorsal and dorsolateral cushion.

With one implementation the proximal and distal inflatable rings have a groove at the position corresponding to area of urethra see FIG. 7. The groove can be used in combination with the projections and/or cushions as described above. However, with one implementation, the distal inflatable ring may only include a groove for the urethra. The groove is kept in place when inflation occurs by the reinforced ventral ends 702 constructed with a stiffening material. The stiffening material can cover the entire outer surface of the ventral ends 702 or the stiffening material may only cover a portion of the outer surface of each ventral end 702. The ends of the ring in the urethral area of penis are reinforced with a stifling material and a stiff bar member 703 bridges the gap between the two stiffened non-contacting ventral ends 702 of the ring. An attachment 704 on each ventral end 702 is obliquely attached between the end of the ring and the stiff bar member in order to further anchor the ends 702 of ring to the bar 704 to prevent the ventral ends 702 of the ring from pushing inwards dorsally. The groove 705 allows the free passage of ejaculate, however, the groove may allow venous outflow from the corpus spongiosum causing loss of erection particularly of the glans. In one implementation as shown in FIG. 8, the ring has an open end in the urethral area such that the inflatable constriction ring as shown in FIG. 8 is not a closed ring.

Figure 9:
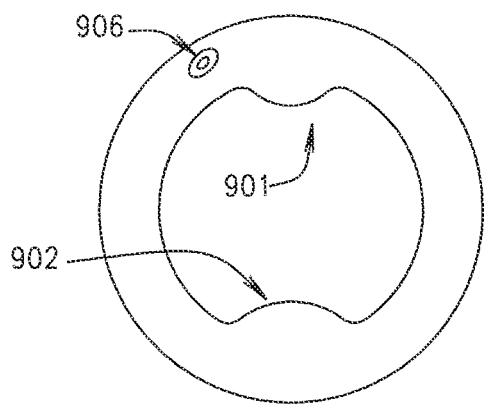
FIG. 9 is a constriction ring with a dorsal and urethral projection.

For one implementation, to address the problem with the groove allowing venous outflow, the urethral groove can be eliminated and replaced with a bulge or cushion 902 at the corpus spongiosum position as shown in FIG. 9. With this implementation, deflation of the inflatable ring is effected by manually operating or controlling remotely the inflation system to facilitate the natural ejaculation. Similarly this implementation can be utilized for both the proximal and distal constriction rings. The tubing of the inflation system is connected to outer surface of inflatable constriction ring. The tubing of the inflation system connected to the distal constriction ring is attached by means of a micro-channel running through the intermediate bar acting as a fluid communication conduit between the tubing and the interior bladder of the inflatable constriction ring.

One implementation of the technology as disclosed herein is to use an inflatable constriction ring in combination with a vacuum chamber stimulation device. For this implementation, a removable sealing element is placed on the proximal end of the vacuum chamber and is formed of a skin compatible material. The opening of the sealing element can vary in diameter to accommodate different penis sizes at the base. One implementation includes a concentric inner seal placed inside a larger seal having an opening with a diameter slightly less than the outer diameter of the concentric inner seal to thereby create a press fit. One purpose for this implementation is to minimize the suction and potential injury to the tissue surrounding the penis base. During operation the seal is secured on the proximal end of the vacuum chamber. The operator's penis is introduced through the seal's central opening, and the seal is placed against the user's body firmly, and a vacuum is produced by the vacuum generating system to evacuate the vacuum chamber. The vacuum chamber stimulating device has a release valve to discharge the vacuum after inflating the constriction ring, which will be discussed further herein. A pressure measurement gauge is installed for both the vacuum chamber stimulating device and the inflatable constriction ring(s).

The vacuum chamber has an opening in its wall at the proximal end close to an edge that contacts the user's body to accommodate an air-tight tubing system. In another embodiment contemplated herein, the opening in the vacuum chamber wall may be disposed adjacent to the seal at the proximal end of the vacuum chamber to accommodate an air-tight tubing system. Alternative embodiments are contemplated that position the opening in the vacuum chamber in varying positions upon the wall of the vacuum chamber.

In one embodiment, an inflatable constriction ring is utilized in combination with the vacuum chamber stimulation device, which includes an inflation mechanism and an inflatable annular ring encircling the base of penis. The outer surface of such ring can be made of non-resilient material and the inner surface can be made of skin compatible non-slippery material. Any material can be used that will provide the inflation constriction mechanism. This ring can be inflated by air or liquid. The other component of the inflatable constriction ring is a manual or battery operated mini-pump, which can be separate from vacuum generation pump. The mini-pump is attached to the inflatable constriction ring by detachable tubing either directly to the inflatable ring or by means of small tubing attached to the ring. The constriction ring has ear-like structures to help put the ring on and off of the penis. Ends of ear-like structure can be placed inside the sealing end of the vacuum chamber to help keep the inflatable ring in position while evacuating the vacuum chamber.

Projections are disposed upon an inner surface of the constriction ring that cover the dorsal and dorsolateral positions of the penis at the base that correspond to the position of penile veins. With one implementation, a ring can have on continuous cushion covering the dorsal and dorsolateral positions of the penis. The cushion at the dorsolateral position may impede the arterial blood flow in the dorsal arteries of a patient requiring high pressure in the ring to control venous leaks; in this situation, just one dorsal cushion may be more beneficial to compress the dorsal vein. The ring has a groove to accommodate the urethra in addition to the abovementioned projections/cushions. Another implementation of the proximal inflatable constriction ring includes dorsolateral and ventrolateral projections to compress the root of the penis diagonally to impede venous outflow from corpora cavernosa. Another implementation of the proximal inflatable constriction ring includes lateral projections to compress the base of the penis from either side and thereby impede venous outflow from the corpora cavernosa.

The groove is kept in place by reinforcing ventral ends with a stiffening material/mechanism. The ends of the ring towards the urethral area of penis are reinforced with the stiffening material and a stiff bar that bridges the gap between the two stiff ends. Two attachments are attached obliquely between the end of the ring and the stiffening bar in order to anchor the ends of the ring to the bar to prevent the ends of the ring from pushing dorsally inwards. The groove allows for the free passage of ejaculate; however, the groove may fail to prevent venous outflow from the corpus spongiosum, thereby causing loss of erectility particularly the glans penis. The urethral groove can therefore be eliminated and replaced with a bulge or cushion at the corpus spongiosum/urethral position. The deflation of a ring is effected by manual or remote control to facilitate ejaculation. The tubing of the inflation system is connected to an outer surface of the proximal inflatable constriction ring.

The tubing connecting the inflatable mini-pumps has a detachment mechanism close to the proximal constriction ring. Part of the tubing that remains attached to the ring also has a deflation release valve that can be used to deflate the constriction ring after use. Alternatively, the tubing may be directly attached to the inflatable constriction ring and the constriction ring itself may include a pressure release valve. The inflatable constriction ring can also be deflated by connecting the tubing for use of the release valve of the mini-pump. The inflatable constriction ring, especially the embodiment having the cushion at the corpus spongiosum position, may be enough to maintain erectility of the corpora cavernosa and corpus spongiosum/glans and a distal constriction ring may not be required as described in other sections.

The mini-pump, connectable for inflation of the inflatable constriction ring, may be incorporated with the main vacuum pump located at the distal end of the vacuum chamber, along with an associated pressure gauge. The tubing of the VICD may be disposed inside or outside of vacuum chamber to connect to the inflatable constriction ring. The tubing can be connected through the opening of the proximal seal/air-tight mechanism as described above in case of having tube placed outside of the vacuum chamber wall. The tubing from the inflation/deflation mechanism may be in the form of a double tubing or a dual channel tubing. The pressure release valve(s) are provided for both the vacuum chamber and the constriction ring to adjust the optimum pressure and attain desired results. In such embodiments, the distal end of the vacuum chamber has a suction pump, a suction release valve and a pressure gauge for the suction chamber and the inflation pump, the pressure release valve and the pressure gauge for the inflatable constriction ring(s).

As discussed herein for other implementations, the advantages of the inflatable constriction device includes that the pressure can be adjusted in the constriction ring. The pressure can be high enough to occlude venous and arterial blood flow completely, if desired. Pressure can be adjusted to allow entry of some arterial blood flow and allow some venous return to mimic a natural erection. This can also prevent the penis from changing color or feeling cold, as typically occurs with latex/rubber constriction devices seen in the art. The blood that fills the penis using the current vacuum constriction devices (VCDs) is of mixed type, i.e. both arterial and regurgitating venous blood.

It is possible to inflate the constriction ring device partially to block the regurgitation venous blood and apply the vacuum slowly to thereby fill the corpora cavernosa with arterial blood. This can be of value in particular for penile rehabilitation following radical prostatectomy and/or pelvic surgery, for example, as this technique would provide more oxygenated blood to the penile tissue. The same technique can be used to increase the in-use duration of the constriction ring, often quoted to be 30 minutes. Patients with varying degrees of erectile dysfunction may adjust the pressure of the Inflatable Constriction Device (ICD) to give them an optimal erection. The ICD can be used in combination with other erection enhancing devices such as a vibratory system or external prosthesis. Other complications associated with current VCD's including pain, bruising, among other issues known in the art, can be reduced and potentially eliminated by using the ICD. The ICD can be used by patients able to get erections but have difficulty maintaining them.

Figure 12:
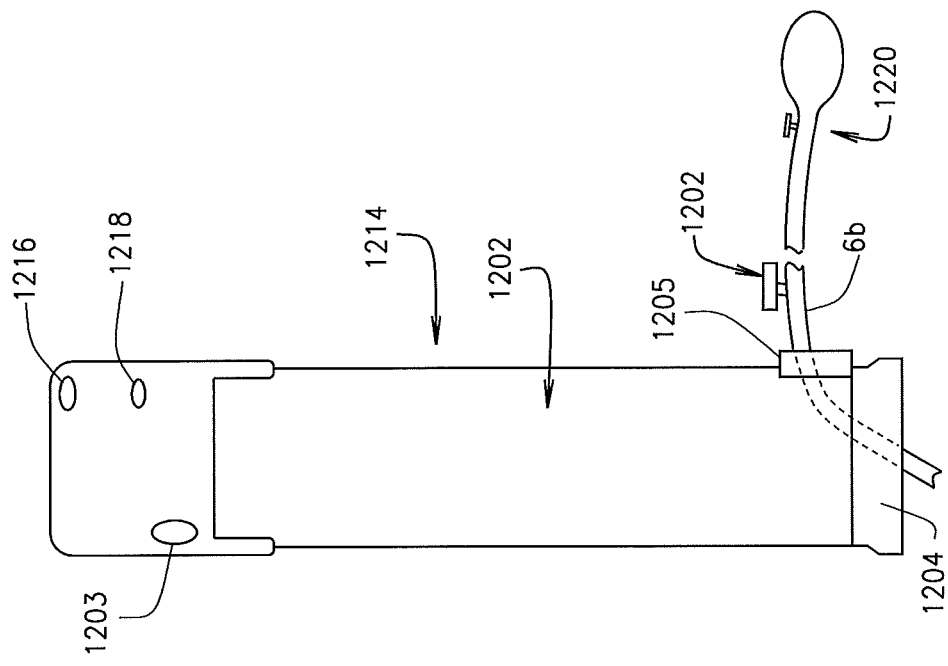
FIG. 12 is a side view of another implementation of a vacuum chamber stimulation device.
Figure 11:
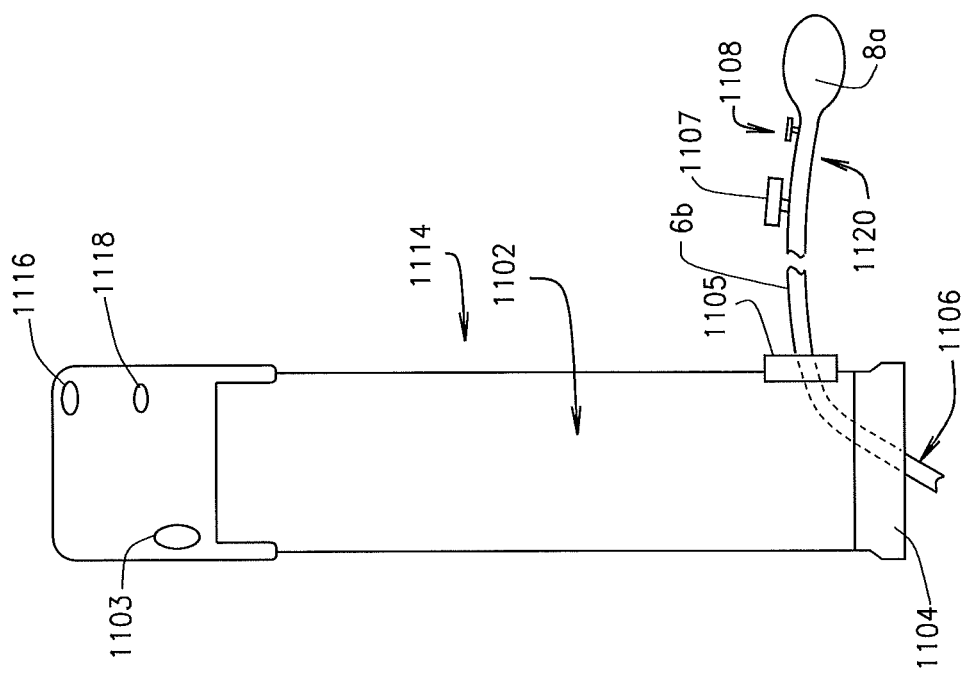
FIG. 11 is a side view of a vacuum chamber stimulation device.

Referring to FIG. 11, a vacuum chamber stimulation device 1114 is shown. The implementation of the vacuum chamber stimulation device as shown includes a vacuum chamber 1102 and an inflation system 1120. One implementation of the apparatus as disclosed herein and as shown in FIG. 11 is a tubular vacuum chamber stimulation device. A vacuum pump 1103 is attached at the distal end of the vacuum chamber 1102. The vacuum pump 1103 may include a power button 1116 that initiates the creation of a vacuum in the vacuum chamber 1102. The vacuum pump 1103 can also include a release valve 1118 that equilibrates the vacuum within the chamber 1102. The vacuum pump 1103 can be manual or powered by a motorized pump. The vacuum chamber stimulation device 1114 also includes a seal 1104 at the proximal end of the vacuum chamber. The seal may be pressed against the user's abdomen (pubis) proximal the base of the penis in order to form a seal. The seal 1104 has a central opening to accommodate the insertion of the user's penis into the vacuum chamber 1102. The side wall of the vacuum chamber 1102 includes an air-tight access portal 1105 through which the tube 1106 of the inflation system 1120 is inserted in order to attach to the inflatable constriction ring. The air-tight access portal 1105 is shown located close to the edge of the proximal end of the vacuum chamber 1102. Referring to FIG. 12, the implementation of the vacuum chamber stimulation device 1214 is practically the same as the implementation illustrated in FIG. 11, except that the air-tight access portal 1205 for the inflation system 1220 is located at the edge of the vacuum chamber proximate the seal 1204. The air-tight part of inflation system 1220 can be removed and replaced by sliding it at the edge of vacuum chamber 1202 after securing the constriction ring at the base of penis and after connecting the tubing. This arrangement may be more convenient for some users.

Figures 13B, 13C:
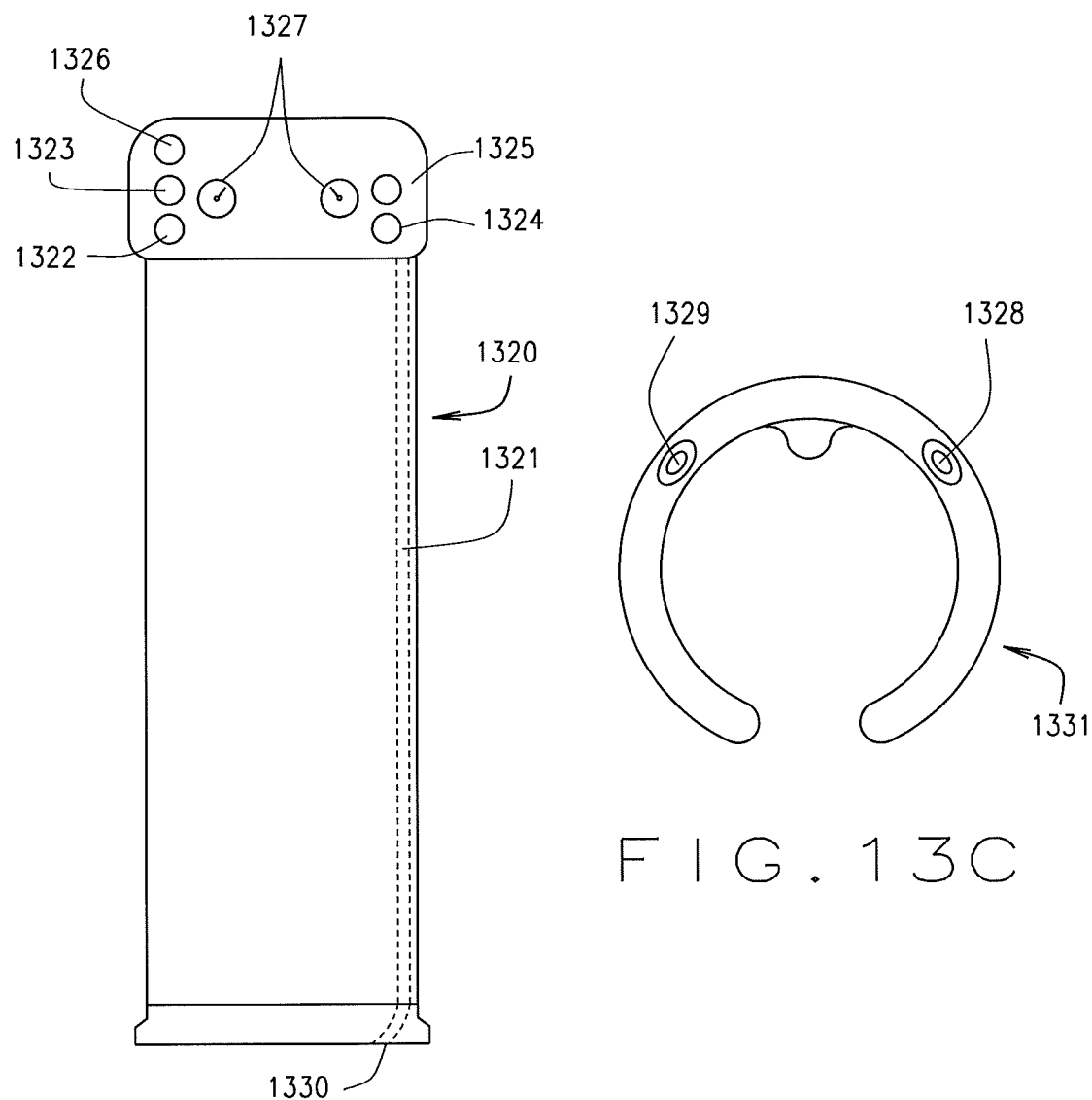
FIG. 13A is a side view of another implementation of a vacuum chamber stimulation device having two pumps.
FIG. 13 B shows inflation/deflation system incorporated at distal end and tubing running along wall of the vacuum chamber.

Referring to FIG. 13A, a dual inflation system is shown where both a proximate inflatable constriction ring and a distal inflatable constriction ring are utilized in combination with a vacuum chamber stimulation device 1314. The implementation of the vacuum chamber stimulation device 1314 as shown includes a vacuum chamber 1302 and inflation systems 1308 and 1309. A vacuum pump 1303 is attached at the distal end of the vacuum chamber 1302. The vacuum pump 1303 can include a power button 1316 that initiates the creation of a vacuum in the vacuum chamber 1302. The vacuum pump 1303 can also include a release valve 1318 that equilibrates the vacuum within the chamber 1302. The vacuum pump 1303 may be manual or it may be powered by a motorized pump. The vacuum chamber stimulation device 1314 also includes a seal 1304 at the proximal end of the vacuum chamber 1302. The seal 1304 can be pressed against the user's abdomen (pubis) proximal the base of the penis in order to form a seal. The seal 1304 has a central opening to accommodate the insertion of the user's penis into the vacuum chamber 1302. The side wall of the vacuum chamber 1302 includes an air-tight access portal 1305 through which tubes 1306 and 1311 of the inflation systems 1308 and 1309 are inserted in order to attach to the inflatable constriction ring. The air-tight access portal 1305 is shown located close to edge of the proximal end of the vacuum chamber 1302. Referring to FIG. 13A, the implementation of the vacuum chamber stimulation device 1314 is practically the same as the implementation illustrated in FIG. 11, except that the air-tight access portal 1305 for the inflation systems includes inflation systems for both a proximal and distal inflatable constriction ring. FIG. 13B shows another implementation having a suction pump 1323, a release pump 1322 for the vacuum chamber 1320, an inflation pump 1325, and a deflation pump 1324 disposed in operational communication with the proximal ring. Pop valve 1326 that is disposed to open in response to excessive negative pressure in the vacuum chamber 1320, and pressure gauges 1327 for pumps that are located at the distal end of the vacuum chamber 1320. The tubing 1321 connecting the inflation and deflation pumps 1324, 1325 at the distal end of the vacuum chamber 1320 with the proximal ring at the base of the penis runs along the wall of vacuum chamber 1320. FIG. 13C shows the proximal ring 1331 with the receiving port 1328 for the inflation/deflation tubing 1321, as mentioned above, and an independent port/knob 1329 to deflate the ring after use. The port/knob 1329 may be manually or remotely controlled. The proximal end 1330 of the tubing 1321 connects with the receiving port 1328 of the ring. FIGS. 13B and 13C are appropriately labeled. As is seen in FIGS. 14 and 15, the outer diameter of the proximal constriction ring is less than the tubular vacuum chamber inner diameter such that there is no sealing relationship between the pliable ring and the tubular vacuum chamber.

FIGS. 14 and 15 illustrate the position of the inflatable constriction ring 1402 in relation to the seal 1404 at the base of the vacuum chamber. The inflatable constriction ring 1402 does not form an air-tight sealable relationship with the interior surface 1502 of the seal 1404. Also, the implementation as disclosed in FIGS. 14 and 15 has the inflation tube 1406 extending through an air-tight conduit 1408 and through the seal 1404 in order to communicably connect to the inflatable constriction ring 1402.

Figure 19:
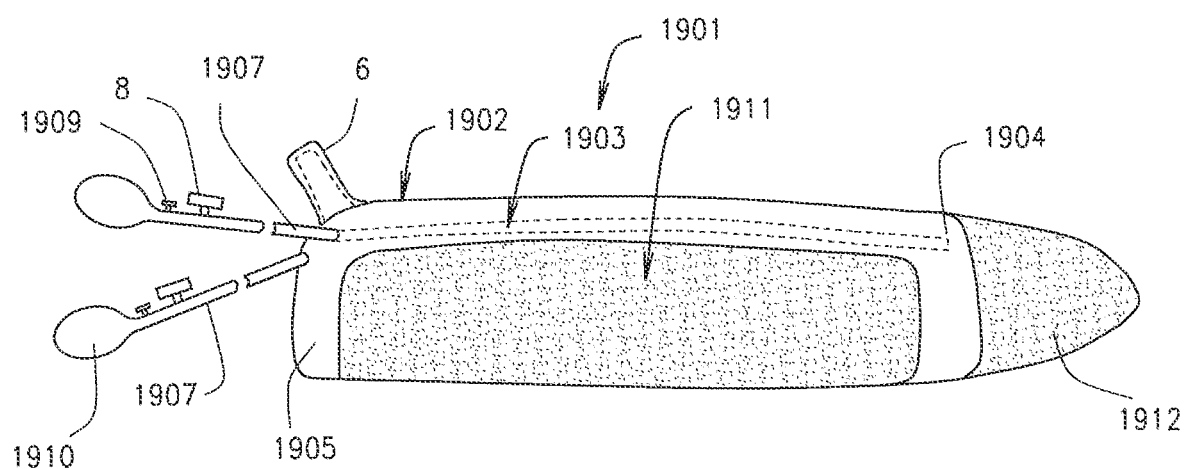
FIG. 19 is a configuration of proximal and distal inflatable constriction rings (ICD) with intermediate band housing the microchannel for distal ICR.

One implementation of the technology 1901 as shown in FIG. 19, is use of the technology in combination with an implanted penile prosthesis wherein an inflatable constriction ring (ICD) is applied at the base of the penis. One implementation includes a proximal inflatable constriction ring 1905 that is attached to the inflation system 1910. The constriction ring 1905 includes an inflatable ring-like structure having an interior bladder communicable with an inflation system and a pliably expandable wall structure containing the interior bladder and forming a ring-like structure. A proximate inflatable annular ring is configured to encircle the base of the user's penis and a distal inflatable ring 1904 is configured to encircle the base of the glans. The proximal and distal rings, 1905 and 1904, are attached by means of an intermediate bar 1902 that houses the microchannel 1903 connecting the distal inflatable ring 1904 to the inflation deflation mechanism 1909.

One implementation of the outer surface of the inflatable ring, opposite to the side that contacts the penis 1911, is made of non-resilient material. The inner surface that contacts the penis is made of a skin compatible, preferably non-slippery material. Any material can be used that will allow for inflation and to provide constriction. This proximate and distal inflatable rings can be inflated by air or liquid. The inflation system that is communicable with the interior bladder is configured to push a flow of air or liquid to fill the bladder and expand at least the inner surface of the inflatable ring to thereby reduce its diameter and apply an inward pressure against the penis to constrict blood flow.

One implementation of the inflatable constriction ring includes a manual or battery operated mini-pump having an outlet port through which air or fluid is forcibly pumped. The outlet port of the mini-pump, in one implementation, is communicably connected to the interior bladder by a tube 1907. The mini-pumps are attached to the inflatable constriction rings by detachable tube 1907 either directly to the inflatable ring or by means of small tubing attached to the annular band above ring.

One implementation of the proximal and distal constriction rings includes an ear-like structure to assist with placing the ring around the penis and removing the ring from the penis. If the technology is utilized in combination with a vacuum chamber, as will be discussed further, the ends of ear-like structure can be placed inside the sealing end of the vacuum chamber to assist with holding the ring in position while initiating the vacuum if so desired.

One implementation of the technology contemplates a constriction ring attached to the inflation system 1910 applied at the base of the penis. The constriction ring includes an inflatable ring-like structure having an interior bladder communicable with the inflation system 1910 and a pliably expandable wall structure containing the interior bladder and forming a ring-like structure. A proximate inflatable annular ring is configured to encircle the base of penis. With one implementation a distal inflatable ring is configured to encircle the base of the glans 1912. The inflation system 1909 can be communicably connected to the distal inflatable constriction ring by way of the microchannel 1903 housed in the intermediate bar 1902.

The proximal inflatable constriction ring 1905 has projections on the inner surface that cover dorsal and dorsolateral positions corresponding to penile veins of the penis proximal the penis base. In another implementation, the ring may have a continuous cushion covering the dorsal and dorsolateral position of the penis to impede venous outflow from the penile veins. The cushion disposed at the dorsolateral position may impede arterial flow in dorsal arteries for a patient in need of high pressure in the ring to control venous leakage. In this situation, just one dorsal cushion may be more beneficial to compress the dorsal vein. One implementation of the proximal inflatable constriction ring includes dorsolateral and ventrolateral projections to compress the base of the penis diagonally to thereby impede venous outflow from corpora cavernosa.

The proximal ring has a groove at a position to accommodate the urethra in addition to the abovementioned projections/cushions; however, the distal inflatable ring has only a groove for urethra. The grooves are maintained in place by ventral ends reinforced with stiffening material/mechanism. The ends of the ring towards the urethral area of the penis are reinforced with stiffening material and a stiff bar that bridges the gap between the two reinforced ends. Two attachments are attached obliquely between the end of the ring and the stiff bar in order to further anchor the ends of ring to the bar to prevent the ends of the ring from pushing inwards dorsally.

The groove allows the free passage of ejaculate, however, a groove may allow venous outflow from the corpus spongiosum causing loss of erection of the glans. As presented herein, to address this problem of venous outflow, the urethral groove can be eliminated and replaced with a bulge or a cushion overlying the corpus spongiosum. An embodiment for deflation of the ring is contemplated as having a manual or a remote control mechanism to facilitate natural ejaculation. A similar arrangement can be made for to include the distal constriction ring. The inflation system tubing is connected to the outer surface of the proximal inflatable constriction ring. The tubing of the inflation system is connected to the distal constriction ring by means of micro-channel running through the intermediate band/bar connecting the proximal and distal rings. The tubing attaching the inflatable mini-pumps to the distal ring has an attachment port close to the proximal constriction ring.

The distal ring arrangement is similar except that the ring is attached to the inflation mechanism by a micro-channel longitudinally disposed through the intermediate bar connecting the proximal and distal rings. The distal ring does not require projections. The urethral groove may be replaced with cushion to impede the venous flow from the glans and manual or remote control release mechanisms may be included to deflate the ring and facilitate natural ejaculation.

The configuration as described may be good with solid malleable implants, but inflatable implants may not tolerate high pressure at the base of the penis. The proximal ring for the base of the penis may be designed without dorsal/dorsolateral cushions to enable use with low pressure. This distal ring, proximal to glans, will mainly provide engorgement of the glans in this situation. This arrangement, combined with the VICD as described, will help attain erectility of residual erectile tissue of the corpora cavernosa and corpus spongiosum/glans.

Figure 18:
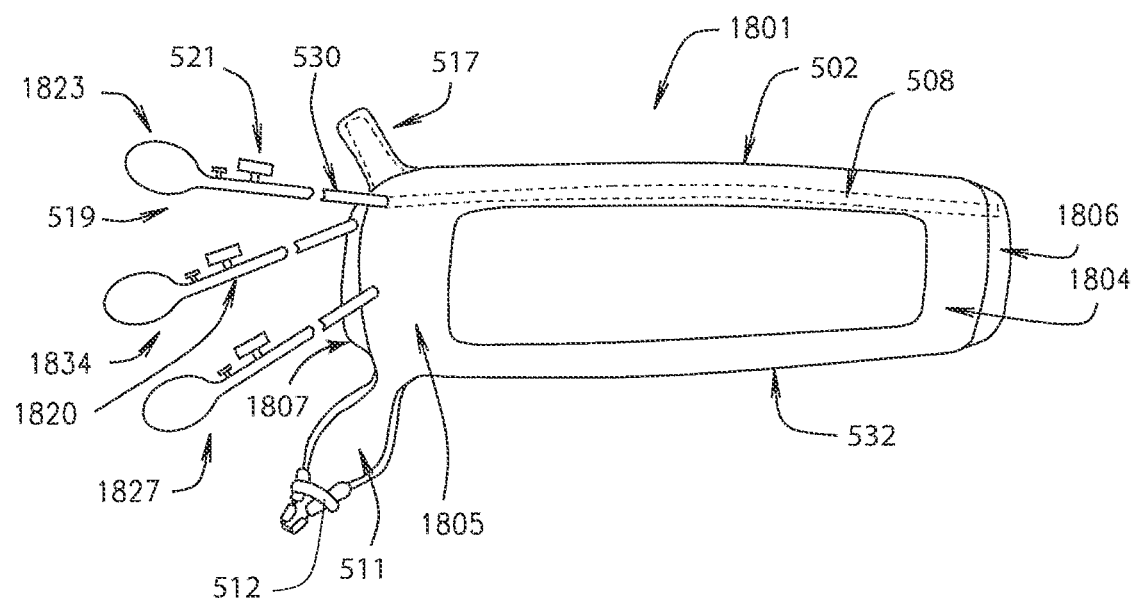
FIG. 18 is an inflatable splint configuration.

One implementation of the present technology includes an inflatable splint 1801. Referring to FIG. 18, the inflatable splint 1801 is shown. One implementation of the inflatable splint includes exterior walls enclosing an interior inflatable bladder. The inflatable splint has its own inflation system 1827. The outer surface can be made of non-resilient material and inner surface can be made of skin compatible, non-slippery material. Any material can be used that will provide the inflation/stiffness. The whole system, excluding the inflatable constriction rings 1806 and 1807, is one cavity or internal bladder that can be inflated by the inflation mechanism 1827, which is like the inflation mechanisms 1823 and 1834 utilized for the inflatable constriction rings. The inflation tubing 1820 is attached to the proximal annular band 1805. All of the system is covered by a skin compatible slippery/smooth material.

Multiple elongated inflatable splints disposed longitudinally in parallel. Annular bands 1804 and 1805 may be attached at the proximal and distal ends of said inflatable splints. One implementation of the technology includes stretchable smaller constriction ring-like structures attached to the abovementioned proximal and distal annular bands to help prevent venous outflow and help keep the device in position. These structures have a non-slippery inner surface. Another implementation of the technology as described has, in lieu of the stretchable smaller ring-like structures attached to the above mentioned proximal and distal annular bands are inflatable constriction rings 1806/1807 to control venous outflow and help anchor the device to the penis as a secondary benefit. As discussed, the venous outflow is a significant factor in causing erectile dysfunction in many middle aged and most elderly patients, and in selected patients at younger age. The inflatable splints may be replaced with a solid, intermediate splint structure, a rigid intermediate splint structure, a pliable intermediate splint structure, or a flexible splint structure.

Similar to other implementations, the constriction ring may include an inflation mechanism; an inflatable annular ring 1807 encircling the base of penis, and an inflatable ring 1806 encircling the base of the glans. The outer surface of such ring may be made of non-resilient material and the inner surface may be made of skin compatible, preferably non-slippery material. Any material can be used that will provide the inflation constriction mechanism. This ring can be inflated by air or liquid. The inflatable constriction ring mechanism includes a manual or a battery powered mini-pump.

Similar to other implementations, the mini-pumps 1823, 1834 are attached to the inflatable constriction rings by detachable tubing either directly to the inflatable rings or by means of small tubing 530 attached above each ring. The proximal inflatable constriction ring has projections on the inner surface that cover the dorsal and dorsolateral position of the penis at the base corresponding to penile veins. Similar to other implementations, one implementation of the ring has a continuous cushion covering the dorsal and dorsolateral position of the penis. The cushion at said dorsolateral position may impede the arterial flow in dorsal arteries in patients requiring high pressure in the ring to control venous leakage. In this situation, just one dorsal cushion may be more beneficial to compress the dorsal vein. One implementation of proximal inflatable constriction ring includes dorsolateral and ventrolateral projections to compress the base of the penis diagonally to impede venous outflow from corpora cavernosa. One implementation of proximal inflatable constriction ring includes shows lateral projections to compress the root of penis to from sides to impede venous outflow from corpora cavernosa.

In one implementation, the proximal ring has a groove at the position corresponding to urethra in addition to the above described projections/cushions, however, the distal inflatable ring has only a groove for accommodating the urethra. The groove is kept in place by ventral ends reinforced with a stiffening material/mechanism. The ends of the ring towards urethral area of the penis are reinforced with stiffening material and a stiff bar that bridges the gap between the two stiff ends. Two attachments are attached obliquely between the ends of the ring and the stiff bar to further anchor the ends of the ring to the bar and prevent the ends of the ring from pushing dorsally inwards. The groove allows the free passage of ejaculate, however, the groove may allow venous outflow from the corpus spongiosum causing a loss of erectility, particularly for the glans. To address the above problem, the urethral groove can be eliminated and replaced with a bulge or cushion at the corpus spongiosum position. Arrangement for deflating the ring may be made by manual or remote control mechanism to facilitate the natural ejaculation by having a deflation port/knob on the ring independent from the inflation deflation ports mentioned elsewhere. Similar arrangements can be made for the distal constriction ring.

The tubing of the inflation system is connected to the outer surface of the proximal inflatable constriction ring. The tubing of the inflation system to the distal constriction ring is attached by means of a micro-channel 508 running through the intermediate bar 502. The tubing attaching to the inflatable mini-pumps has a detachment mechanism close to the proximal constriction ring and part of the tubing that remains attached to the ring also has a deflation release valve that can be used to deflate the constriction ring after use. Alternatively, detachable tubing can be directly attached to the inflatable ring in the case of the proximal ring and the constriction ring may have pressure release valve.

The constriction ring can also be deflated by connecting the detached tubing and using the release valve of the mini-pump. After inflating the rings optimally, the tubing is detached and part of tubing attached to constriction ring-stumps is stored in a small pocket 517 attached to ring to prevent injury from loose ends during intimate contact. The tubing of the inflation mechanism for the inflatable constriction ring also has a pressure measuring gauge 521 to measure the pressure in the inflatable constriction ring. The proximal constriction ring, especially the embodiment having the cushion at the corpus spongiosum position, may be enough to maintain erection of the corpora cavernosa and corpus spongiosum/glans penis, therefore the distal constriction ring may not be necessary.

As described for other implementations herein, a stretchable beaded ring on the proximal annular band 511 of the device is included, by means of which the testicles can be attached to the device. A small tightening ring 512 is threaded over the beaded ring to tighten or loosen the beaded ring around the testicles of the user. This arrangement gives the support for the apparatus in use. As a result of the stiffness imparted by the external splints encased in the flexible skin-compatible material, the device can provide an erection for an individual with erectile dysfunction sufficient to engage in sexual intercourse. If it is not possible to get an erection naturally, one can apply the vibratory devices as described in contemplation of other implementations herein or the device can be used with the Vacuum Inflatable Constriction Device (VICD) designed for achieving and maintaining an erection. The inflation mechanism etc. can be arranged similar to other described implementations. Yet another implementation can include an elongated vibratory unit that extends longitudinally substantially along the entire length of an inflatable splint. An added advantage of this embodiment of the device is that it increases the circumference of the penis over almost the entire length of the penis.

Figure 16:
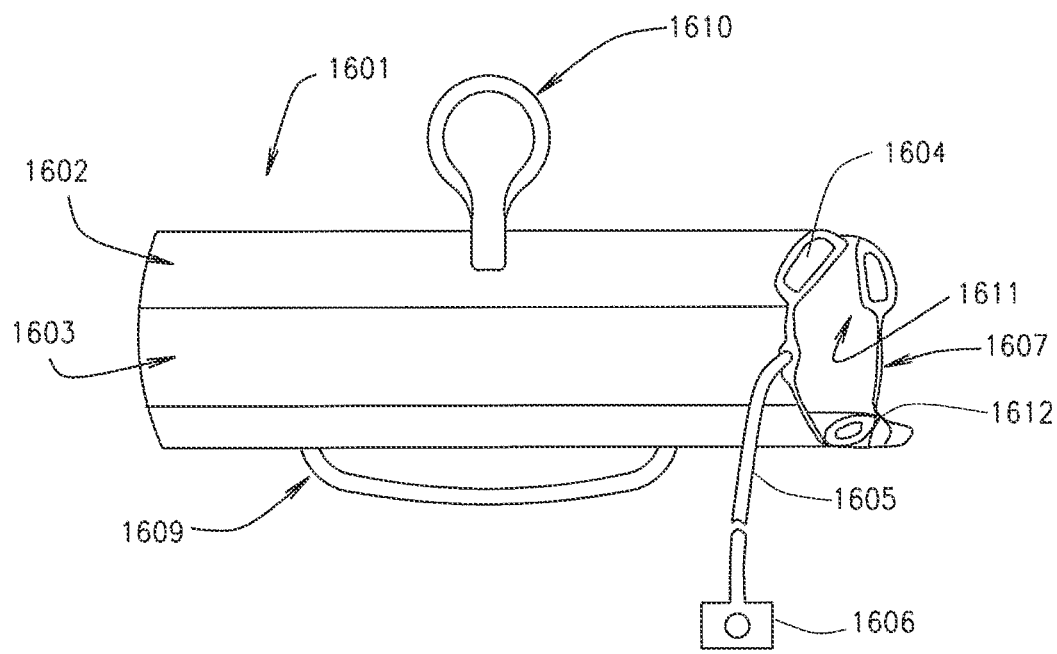
FIG. 16 is a side view of a vibrator sleeve.
Figure 17:
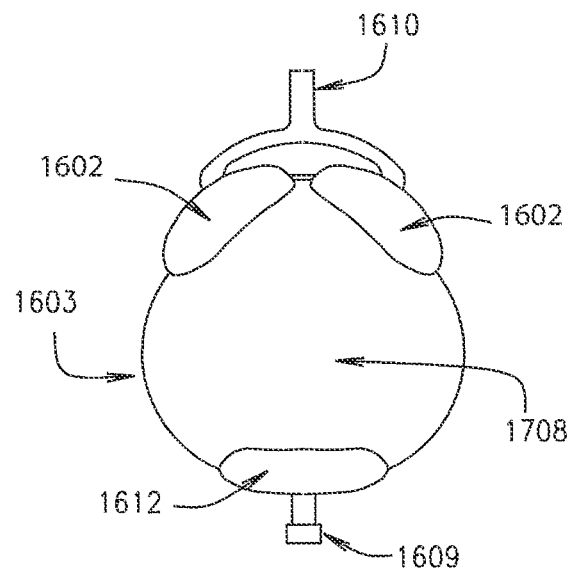
FIG. 17 is a sectional view of the vibrator sleeve.

One implementation of the present technology includes a vibrator sleeve. Referring to FIGS. 16 and 17 a vibrator sleeve 1601 is shown. The vibration stimulation of the penis is achieved by an elongated tubular vibrator sleeve 1607 with two elongated dorsolateral vibrators 1604 connected in a side-by-side relationship by web or membrane members 1603 thereby forming a sleeve-like structure as illustrated in FIG. 16. The elongated housing 1602 containing the elongated vibrator unit 1604 can be made of non-resilient material or a pliable material and the inner surface 1611 is made of skin-compatible non-slippery material. The whole vibrator system includes dual dorsolateral elongated vibrator units 1604, and in one implementation as shown, a ventral elongated vibrator unit 1612 is included. The ventral vibrator 1612 has an extension to cover and stimulate the frenulum of the penis. The above vibratory units 1604, 1612 stimulate the branches of the dorsal nerve and the perennial nerve. Additional vibratory units may be placed if required. The intervening web or membrane members 1603 between the vibratory units is thin and stretchable. Handles 1610 and 1609 can be used to assist in sliding the sleeve 1601 over the penis 1708 as well to urge the vibrator units against the surface of the penis. The vibration control unit is powered and has a controller and transmitter. The controller is configured to control the transmitter to transmit control signals to the vibrator units to power them on as well as control the level of vibration desirably applied.

The device can also be used for diagnostic purposes to investigate the effect of vibration on penile blood flow. The proximal annular band is removed at the ventrolateral aspect in order to gain an access for Duplex ultrasound probe to cavernosal artery close to the base of penis. The device is held in position by mean of an elastic band wrapped around the device surrounding the penis during the diagnostic procedure.

The aim of this invention is to provide stimulation by means of vibration applied to penis. This device can be used for penile rehabilitation and by an individual with erectile dysfunction who needs or prefers to use vibration but does not want to wear vibratory devices during intercourse. These patients can attain an erection by vibratory stimulation and may or may not need additional assistive devices as described in other sections.

Figure 20B:
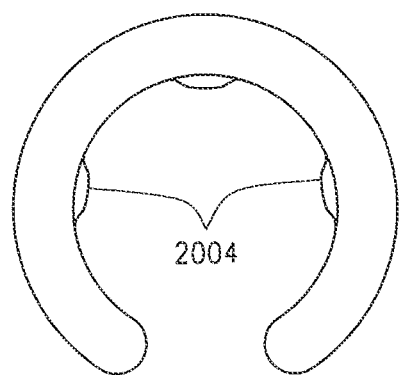
Figure 20C:
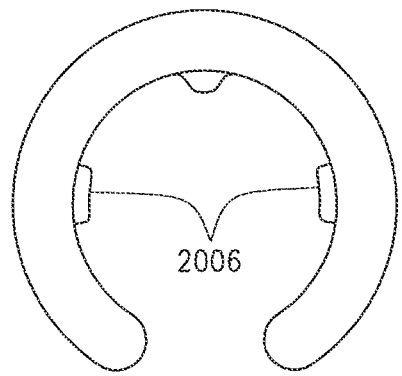

Referring to FIGS. 20A, 20B, 20C, different configurations of the projections on the inflatable constriction device (ICD) or pliable constriction ring structures are illustrated. Referring to FIG. 20A, the dorsal projection 2001 causes pressure on the dorsal vein to impede venous outflow. Referring to FIG. 20A, the dorsolateral and ventrolateral projections 2002, 2003, which project diametrically inward to compress the base of the penis diagonally to impede venous outflow from the corpora cavernosa. Referring to FIG. 20B, diametrically opposing lateral projections 2004 compress the base of the penis to from sides to impede venous outflow from corpora cavernosa. Referring to FIG. 20C, lateral projections 2006 compress the base of the penis from the sides to impede venous outflow from corpora cavernosa, but have a different shape. One implementation of the constriction ring as shown in FIGS. 20A-20C is an inflatable constriction ring including an exterior wall enclosing an interior bladder and configured such that the interior portion of the ring diametrically expands inwardly to thereby apply an inward pressure or force against the skin of the user.

The various implementations and examples shown above illustrate a method and apparatus for constricting blood flow and providing stimulus to the penis of a user. A user of the present method and apparatus may choose any of the above implementations, or an equivalent thereof, depending upon the desired application. In this regard, it is recognized that various forms of the subject constriction and stimulus method and apparatus could be utilized without departing from the scope of the present technology and the various implementations as disclosed.

As is evident from the foregoing description, certain aspects of the present implementation are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the scope of the present implementation(s) set forth herein. Accordingly, the specification and drawings are to be regarded in an illustrative rather than a restrictive sense.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the detailed description, with each claim standing on its own as a separate embodiment.

The various implementations and examples shown above illustrate a method and apparatus for addressing erectile dysfunction. A user of the present technology as disclosed may choose any of the above implementations, or an equivalent thereof, depending upon the desired application. In this regard, it is recognized that various forms of the subject erectile dysfunction device could be utilized without departing from the scope of the present invention.

Other aspects, objects, and advantages of the present technology as disclosed can be obtained from a study of the drawings, the disclosure and the appended claims.

What is claimed is:

1. An apparatus for addressing erectile dysfunction comprising:
   a proximal annular band attached to a proximate end of an elongated intermediate bar;
   a distal annular band attached to a distal end of the elongated intermediate bar; and
   a proximal pliable constriction ring structure attached to the proximal annular band;
   wherein the proximal pliable constriction ring structure has diameter less than a of the proximal annular band.

2. The apparatus as recited in claim 1 further comprising:
   a distal pliable constriction ring structure attached to the distal annular band wherein a diameter of the distal pliable constriction ring structure is less than a diameter of the distal annular band.

3. The apparatus as recited in claim 2 wherein the distal pliable constriction ring structure includes both a dorsal and a dorsolateral projection that project diametrically inward to compress veins.

4. The apparatus as recited in claim 3 wherein the distal pliable constriction ring structure includes a ventrolateral projection that projects diametrically inward from a ventrolateral position on an interior of the distal pliable constriction ring structure.

5. The apparatus as recited in claim 4 wherein the distal pliable constriction ring structure includes a ventral groove in a position devised to avoid compression of a wearer's urethra.

6. The apparatus as recited in claim 5 wherein the distal pliable constriction ring structure is inflatable.

7. The apparatus as recited in claim 2 wherein the distal pliable constriction ring structure is inflatable.

8. The apparatus as recited in claim 7 further comprising:
   a micro-channel extending through the intermediate bar communicably linking an inflation device and the distal constriction ring structure.

9. The apparatus as recited in claim 7 further comprising:
   an elongated vibrator unit housed by the elongated intermediate bar, said vibrator unit extending longitudinally along substantially an entire length of the elongated intermediate bar.

10. The apparatus as recited in claim 2 further comprising:
    an elongated vibrator unit housed by the elongated intermediate bar, said vibrator unit extending longitudinally along substantially an entire length of the elongated intermediate bar.

11. The apparatus as recited in claim 1 wherein the proximal pliable constriction ring structure includes both a dorsal and dorsolateral projection that project diametrically inward from dorsal and dorsolateral positions on an interior of the proximal pliable ring structure to compress veins.

12. The apparatus as recited in claim 11 wherein the proximal pliable constriction ring structure includes a ventrolateral projection that projects diametrically inward from a ventrolateral position on the interior of the ring.

13. The apparatus as recited in claim 12 wherein the proximal pliable constriction ring structure includes a ventral groove in a position devised to avoid compression of a wearer's urethra.

14. The apparatus as recited in claim 13 wherein the proximal pliable constriction ring structure is inflatable.

15. The apparatus as recited in claim 1 wherein the proximal pliable constriction ring structure is inflatable.

16. The apparatus as recited in claim 15 further comprising:
    an elongated vibrator unit housed by the elongated intermediate bar, said vibrator unit extending longitudinally along substantially an entire length of the elongated intermediate bar.

17. The apparatus as recited in claim 2 wherein the elongated intermediate bar is configured to be positioned along a dorsal area of a penis.

18. The apparatus as recited in claim 17 further comprising:
    an opposing elongated intermediate bar having a proximal opposing end attached to the proximal annular band and a distal opposing end attached to the distal annular band.

19. The apparatus as recited in claim 18 further comprising:
    an opposing elongated vibrator unit housed by the opposing elongated intermediate bar, said opposing elongated vibrator unit extending longitudinally along substantially an entire length of the opposing elongated intermediate bar.

20. The apparatus as recited in claim 1 further comprising:
    an elongated vibrator unit housed by the elongated intermediate bar, said vibrator unit extending longitudinally along substantially an entire length of the elongated intermediate bar.

21. The apparatus as recited in claim 1 wherein the elongated intermediate bar is configured to be positioned along a dorsal area of a penis.

22. The apparatus as recited in claim 21 further comprising:
    an opposing elongated intermediate bar having a proximal opposing end attached to the proximal annular band and a distal opposing end attached to the distal annular band.

23. The apparatus as recited in claim 22 further comprising:
    an opposing elongated vibrator unit housed by the opposing elongated intermediate bar, said opposing elongated vibrator unit extending longitudinally along substantially an entire length of the opposing elongated intermediate bar.

24. A system for addressing erectile dysfunction comprising:
    a tubular vacuum chamber stimulation device usable to instantiate a vacuum over a penis of a user;
    a seal disposed upon a proximal end of the tubular vacuum chamber stimulation device configured to sealably contact the user; and
    a proximal pliable constriction ring structure coaxially positioned with respect to the tubular vacuum chamber stimulation device, wherein an outer diameter of the proximal pliable constriction ring structure is less than an inner diameter of a tubular vacuum chamber of the tubular vacuum chamber stimulation device;
    wherein the proximal pliable constriction ring structure is configured to not sealably contact the vacuum chamber.

25. The system as recited in claim 24 further comprising:
    a distal pliable constriction ring structure disposed coaxially with respect to the tubular vacuum chamber stimulation device, said distal pliable ring structure having an outer diameter that is less than the tubular vacuum chamber inner diameter wherein the distal pliable constriction ring structure does not sealably contact the vacuum chamber.

26. The system as recited in claim 25 wherein the distal pliable constriction ring structure is inflatable.

27. The system as recited in claim 24 wherein the proximal pliable constriction ring structure is inflatable.

28. The system as recited in claim 27 further comprising:
an inflation pump integrated with the tubular vacuum chamber at a distal end of the tubular vacuum chamber;
a microchannel extending along a wall of the tubular vacuum chamber; and
a receiving port disposed upon the proximal pliable constriction ring structure, said receiving port configured to interconnect with the microchannel when the tubular vacuum chamber is placed overtop the proximal pliable constriction ring structure;
wherein the microchannel communicably connects the proximal pliable constriction ring structure with the inflation pump.

29. The system as recited in claim 24 wherein the vacuum chamber further comprises an airtight access portal through which at least one tube is insertable for connection to the proximal pliable constriction ring structure to inflate the proximal pliable constriction ring structure.

30. An apparatus for addressing erectile dysfunction configured for use in conjunction with a tubular vacuum chamber and connectable to tubing disposed in fluid communication with an inflation pump and a deflation pump disposed in the tubular vacuum chamber, said apparatus comprising:
an inflatable proximal pliable constriction ring inflatable by action of the inflation pump when the tubular vacuum chamber is positioned to connect the tubing with the inflatable proximal pliable constriction ring and the inflation pump is activated;
an inflatable distal pliable constriction ring inflatable by action of the inflation pump when the tubular vacuum chamber is positioned to connect the tubing with the inflatable proximal pliable constriction ring and the inflation pump is activated;
an inflatable elongated pliable intermediate splint structure having a proximal end attached to the proximal constriction ring, said intermediate splint structure extending longitudinally to a distal end that is attached to the distal pliable constriction ring; and
a plurality of secondary intermediate splint structures positioned laterally side-by-side and adjacent to the elongated pliable intermediate splint structure, said plurality of secondary intermediate splint structures attached between the proximal and distal constriction rings.

31. The apparatus as recited in claim 30 wherein the plurality of secondary intermediate splint structures is inflatable and is laterally interconnected side by side, each of said plurality of secondary intermediate splint structures having exterior walls enclosing an interior inflatable bladder.

32. An apparatus for addressing erectile dysfunction comprising:
a plurality of elongated, hollow splint structures, each elongated, hollow splint structure having a pair of lateral edges; and
an elongated vibrator unit housed in each of the elongated splint structures, each elongated vibrator unit extending longitudinally along substantially an entire length of each of the plurality of elongated splint structures;
wherein each of the elongated hollow splint structures is laterally interconnected side by side along both lateral edges by thin stretchable membrane members to adjacent splint structures to form an elongated tubular structure having a central lumen configured for position around a penis of a wearer and wherein each elongated vibrator unit is configured to provide a vibration stimulus to the wearer.

33. The apparatus as recited in claim 32 wherein one of the plurality of elongated splint structures is positioned lengthwise along one or more of a dorsal, dorsolateral, lateral and ventral position.

34. The apparatus as recited in claim 33 further comprising:
an upper holding handle dorsally attached and sufficiently sized for insertion of a thumb; and
a lower holding handle ventrally attached and sufficiently sized for insertion of two or more fingers.

35. The apparatus as recited in claim 34 wherein a pliable extension extends from a distal end of the elongated tubular structure for Frenulum stimulation.

36. A system for addressing erectile dysfunction comprising:
an apparatus comprising:
a proximal annular band, said proximal annual band having a diameter;
a distal annular band, said distal annular band having a diameter;
an elongated intermediate bar interconnecting the proximal and distal annular bands;
a proximal pliable constriction ring structure attached to the proximal annular band, said proximal pliable constriction ring structure having a diameter less than the diameter of the proximal annular band; and
a tubular vacuum chamber configured to seat over top the apparatus;
wherein the proximal annular band diameter is less than an inner diameter of the tubular vacuum chamber.

37. The system as recited in claim 36 wherein the proximal pliable constriction ring structure is inflatable.

38. The system as recited in claim 37 wherein the vacuum chamber further comprises an airtight access portal through which at least one tube is insertable for connection of an inflation pump to the proximal pliable constriction ring structure to inflate the proximal pliable constriction ring structure.

39. The system as recited in claim 37 further comprising:
an inflation pump integrated with the tubular vacuum chamber at a distal end of the tubular vacuum chamber;
a microchannel extending along a wall of the tubular vacuum chamber; and
a receiving port disposed upon the proximal pliable constriction ring structure, said receiving port configured to interconnect with the microchannel when the tubular vacuum chamber is placed overtop the proximal pliable constriction ring structure;
wherein the microchannel communicably connects the proximal pliable constriction ring structure with the inflation pump.

40. The system as recited in claim 36 wherein the elongated intermediate bar comprises:
a vibratory unit;
an inflatable splint mechanism;
a rigid bar; or
a flexible bar.

41. The system as recited in claim 36 further comprising a distal pliable constriction ring structure attached to the distal annular band, said distal pliable constriction ring structure having a diameter less than the diameter of the distal annular band.

42. The system as recited in claim 41 wherein the distal pliable constriction ring structure is inflatable.

43. The system as recited in claim 36 wherein the tubular vacuum chamber does not sealably contact the proximal annular band.

44. The system as recited in claim 41 wherein the tubular vacuum chamber does not sealably contact the proximal or the distal annular band.

* * * * *